(12) United States Patent
Harshman

(10) Patent No.: US 10,433,838 B2
(45) Date of Patent: Oct. 8, 2019

(54) METHODS AND DEVICES FOR FORMING A TISSUE FOLD

(71) Applicant: ENDOGASTRIC SOLUTIONS, INC., Redmond, WA (US)

(72) Inventor: Scott Harshman, Kirkland, WA (US)

(73) Assignee: ENDOGASTRIC SOLUTIONS, INC., Redmond, WA (US)

( * ) Notice: Subject to any disclaimer, the term of this patent is extended or adjusted under 35 U.S.C. 154(b) by 347 days.

(21) Appl. No.: 14/558,496

(22) Filed: Dec. 2, 2014

(65) Prior Publication Data

US 2015/0112365 A1 Apr. 23, 2015

Related U.S. Application Data

(62) Division of application No. 12/383,109, filed on Mar. 18, 2009, now Pat. No. 8,906,037.

(51) Int. Cl.
| | | |
|---|---|---|
| *A61B 17/072* | (2006.01) | |
| *A61B 17/00* | (2006.01) | |
| *A61B 17/04* | (2006.01) | |
| *A61B 17/064* | (2006.01) | |
| *A61B 17/068* | (2006.01) | |
| *A61B 17/08* | (2006.01) | |

(52) U.S. Cl.
CPC ...... *A61B 17/072* (2013.01); *A61B 17/00234* (2013.01); *A61B 17/0401* (2013.01); *A61B 17/064* (2013.01); *A61B 17/068* (2013.01); *A61B 2017/00349* (2013.01); *A61B 2017/00818* (2013.01); *A61B 2017/00827* (2013.01); *A61B 2017/0409* (2013.01); *A61B 2017/0419* (2013.01); *A61B 2017/0464* (2013.01); *A61B 2017/0496* (2013.01); *A61B 2017/0649* (2013.01); *A61B 2017/07214* (2013.01); *A61B 2017/081* (2013.01)

(58) Field of Classification Search
CPC .... A61B 17/00234; A61B 2017/00818; A61B 2017/00827; A61B 17/29; A61B 17/072; A61B 2017/2926
USPC .......................................... 606/139, 142, 143
See application file for complete search history.

(56) References Cited

U.S. PATENT DOCUMENTS

| | | |
|---|---|---|
| 2,753,870 A | 7/1956 | Muffly |
| 3,875,928 A | 4/1975 | Angelchik |

(Continued)

FOREIGN PATENT DOCUMENTS

| | | |
|---|---|---|
| EP | 252607 A2 | 9/1992 |
| WO | 1999022649 A2 | 5/1999 |

(Continued)

OTHER PUBLICATIONS

The gastroesophageal flap valve: in vitro and in vivo observations; Lucius D. Hill et al.; Gastrointestinal Endoscopy; vol. 44, No. 5, 1996; pp. 541-547; abstract.

(Continued)

*Primary Examiner* — Dianne Dornbusch
(74) *Attorney, Agent, or Firm* — Fulwider Patton LLP

(57) ABSTRACT

A device for forming a tissue fold includes a recess and an opening at the end of the recess. Tissue is drawn into the recess and through the opening using a tissue engaging element. As the tissue is drawn through the opening, the tissue layers are compressed together. A fastener is used to secure the tissue fold.

10 Claims, 4 Drawing Sheets

(56) References Cited

U.S. PATENT DOCUMENTS

| | | |
|---|---|---|
| 4,006,747 A | 2/1977 | Kronenthal |
| 4,271,828 A | 6/1981 | Angelchik |
| 4,576,772 A | 3/1986 | Carpenter et al. |
| 4,595,007 A | 6/1986 | Mericle |
| 4,669,473 A | 6/1987 | Richards et al. |
| 4,696,300 A | 9/1987 | Anderson |
| 4,846,836 A | 7/1989 | Reich |
| 4,895,148 A | 1/1990 | Bays et al. |
| 4,921,479 A | 5/1990 | Grayzel |
| 5,006,106 A | 4/1991 | Angelchik et al. |
| 5,041,129 A | 8/1991 | Hayhurst et al. |
| 5,080,543 A | 1/1992 | Murphy |
| 5,088,979 A | 2/1992 | Filipi et al. |
| 5,254,126 A | 10/1993 | Filipi et al. |
| 5,314,473 A | 5/1994 | Godin |
| 5,403,326 A | 4/1995 | Harrison et al. |
| 5,411,508 A | 5/1995 | Bessler et al. |
| 5,411,520 A | 5/1995 | Nash et al. |
| 5,549,621 A | 8/1996 | Bessler et al. |
| 5,571,074 A | 11/1996 | Buckman et al. |
| 5,571,116 A | 11/1996 | Bolanos et al. |
| 5,626,614 A | 5/1997 | Hart |
| 5,676,674 A | 10/1997 | Bolanos et al. |
| 5,713,903 A | 2/1998 | Sander et al. |
| 5,759,151 A | 6/1998 | Sturges |
| 5,810,882 A | 9/1998 | Bolduc et al. |
| 5,814,054 A | 9/1998 | Kortenbach et al. |
| 5,861,036 A | 1/1999 | Godin |
| 5,879,372 A | 3/1999 | Bartlett et al. |
| 5,887,594 A | 3/1999 | LoCicero |
| 5,897,562 A | 4/1999 | Bolanos et al. |
| 5,938,668 A | 8/1999 | Scirica et al. |
| 6,086,600 A * | 7/2000 | Kortenbach ........ A61B 1/00087 606/139 |
| 6,098,629 A | 8/2000 | Johnson et al. |
| 6,113,609 A | 9/2000 | Adams |
| 6,113,611 A | 9/2000 | Allen et al. |
| 6,142,957 A | 11/2000 | Diamond et al. |
| 6,254,642 B1 | 7/2001 | Taylor |
| 6,264,700 B1 | 7/2001 | Kilcoyne et al. |
| 6,302,311 B1 | 10/2001 | Adams et al. |
| 6,302,917 B1 | 10/2001 | Dua et al. |
| 6,312,437 B1 | 11/2001 | Kortenbach |
| 6,315,789 B1 | 11/2001 | Cragg |
| 6,419,669 B1 | 7/2002 | Frazier et al. |
| 6,428,548 B1 | 8/2002 | Durgin et al. |
| 6,447,524 B1 | 9/2002 | Knodel et al. |
| 6,743,239 B1 | 6/2004 | Kuehn et al. |
| 6,773,440 B2 | 8/2004 | Gannoe et al. |
| 6,773,441 B1 | 8/2004 | Laufer et al. |
| 6,790,214 B2 * | 9/2004 | Kraemer ............ A61B 17/0644 606/142 |
| 6,835,200 B2 | 12/2004 | Laufer et al. |
| 6,916,332 B2 | 7/2005 | Adams |
| 6,921,361 B2 | 7/2005 | Suzuki et al. |
| 7,022,118 B2 | 4/2006 | Ariura et al. |
| 7,037,344 B2 | 5/2006 | Kagan et al. |
| 7,074,229 B2 | 7/2006 | Adams et al. |
| 7,083,630 B2 | 8/2006 | DeVries et al. |
| 7,220,266 B2 | 5/2007 | Gambale |
| 7,347,863 B2 | 3/2008 | Rothe et al. |
| 7,618,426 B2 | 11/2009 | Ewers et al. |
| 7,632,287 B2 | 12/2009 | Baker et al. |
| 7,678,123 B2 | 3/2010 | Chanduszko |
| 7,713,277 B2 | 5/2010 | Laufer et al. |
| 7,776,057 B2 | 8/2010 | Laufer et al. |
| 7,811,295 B2 * | 10/2010 | Kortenbach ......... A61B 17/064 606/139 |
| 7,850,704 B2 | 12/2010 | Burnett et al. |
| 7,857,184 B2 | 12/2010 | Viola |
| 7,857,823 B2 | 12/2010 | Laufer et al. |
| 7,860,555 B2 * | 12/2010 | Saadat ................. A61B 1/0008 600/101 |
| 7,866,526 B2 | 1/2011 | Green et al. |
| 7,918,787 B2 * | 4/2011 | Saadat ................. A61B 1/0008 600/127 |
| 7,942,887 B2 | 5/2011 | Kraemer et al. |
| 7,951,157 B2 | 5/2011 | Gambale |
| 7,954,687 B2 | 6/2011 | Zemlok et al. |
| 7,955,340 B2 | 6/2011 | Michlitsch et al. |
| 8,057,494 B2 | 11/2011 | Laufer et al. |
| 8,252,009 B2 | 8/2012 | Weller et al. |
| 8,277,468 B2 | 10/2012 | Laufer et al. |
| 8,308,765 B2 | 11/2012 | Saadat et al. |
| 8,343,175 B2 | 1/2013 | Ewers et al. |
| 8,574,243 B2 | 11/2013 | Saadat et al. |
| 2002/0022853 A1 | 2/2002 | Swanson et al. |
| 2002/0035370 A1 | 3/2002 | Kortenbach |
| 2002/0040226 A1 | 4/2002 | Laufer et al. |
| 2002/0055772 A1 | 5/2002 | McGuckin, Jr. et al. |
| 2002/0072761 A1 | 6/2002 | Abrams et al. |
| 2002/0078967 A1 | 6/2002 | Sixto, Jr. et al. |
| 2002/0082621 A1 | 6/2002 | Schurr et al. |
| 2002/0143349 A1 | 10/2002 | Gifford, III et al. |
| 2002/0183765 A1 | 12/2002 | Adams |
| 2002/0198541 A1 | 12/2002 | Smith et al. |
| 2003/0023230 A1 | 1/2003 | Lewis et al. |
| 2003/0055442 A1* | 3/2003 | Laufer ............... A61B 17/0401 606/153 |
| 2003/0065340 A1* | 4/2003 | Geitz ................. A61B 17/0643 606/151 |
| 2003/0065359 A1 | 4/2003 | Weller et al. |
| 2003/0093117 A1 | 5/2003 | Saadat |
| 2003/0120289 A1* | 6/2003 | McGuckin, Jr. ...... A61B 17/072 606/151 |
| 2003/0120292 A1 | 6/2003 | Park et al. |
| 2003/0171760 A1 | 9/2003 | Gambale |
| 2003/0187465 A1 | 10/2003 | Bailly et al. |
| 2003/0191497 A1 | 10/2003 | Cope |
| 2003/0216613 A1 | 11/2003 | Suzuki et al. |
| 2003/0216754 A1 | 11/2003 | Kraemer et al. |
| 2003/0220657 A1 | 11/2003 | Adams |
| 2004/0044304 A1 | 3/2004 | Hill et al. |
| 2004/0044364 A1 | 3/2004 | DeVries et al. |
| 2004/0087976 A1 | 5/2004 | DeVries et al. |
| 2004/0093024 A1 | 5/2004 | Lousararian et al. |
| 2004/0116949 A1 | 6/2004 | Ewers et al. |
| 2004/0133236 A1 | 7/2004 | Chanduszko |
| 2004/0138529 A1 | 7/2004 | Wiltshire et al. |
| 2004/0147958 A1 | 7/2004 | Lam et al. |
| 2004/0148034 A1 | 7/2004 | Kagan et al. |
| 2004/0153102 A1 | 8/2004 | Therin et al. |
| 2004/0153103 A1 | 8/2004 | Schwartz et al. |
| 2004/0162568 A1 | 8/2004 | Saadat et al. |
| 2004/0215216 A1 | 10/2004 | Gannoe et al. |
| 2004/0236357 A1 | 11/2004 | Kraemer et al. |
| 2004/0243223 A1 | 12/2004 | Kraemer et al. |
| 2005/0004575 A1 | 1/2005 | Sgro et al. |
| 2005/0017781 A1 | 1/2005 | Honda |
| 2005/0043759 A1 | 2/2005 | Chanduszko |
| 2005/0075653 A1 | 4/2005 | Saadat et al. |
| 2005/0085829 A1* | 4/2005 | Kraemer ............... A61B 17/068 606/142 |
| 2005/0154405 A1 | 7/2005 | Kraemer et al. |
| 2005/0177176 A1 | 8/2005 | Gerbi et al. |
| 2005/0187565 A1 | 8/2005 | Baker et al. |
| 2005/0203547 A1 | 9/2005 | Weller et al. |
| 2005/0216040 A1 | 9/2005 | Gertner et al. |
| 2005/0228413 A1 | 10/2005 | Binmoeller et al. |
| 2005/0247320 A1 | 11/2005 | Stack et al. |
| 2005/0251162 A1* | 11/2005 | Rothe .................. A61B 1/0014 606/153 |
| 2005/0251176 A1 | 11/2005 | Swanstrom et al. |
| 2006/0009789 A1 | 1/2006 | Gambale |
| 2006/0135971 A1* | 6/2006 | Swanstrom .......... A61B 1/0014 606/153 |
| 2006/0190018 A1 | 8/2006 | Baker et al. |
| 2006/0253130 A1 | 11/2006 | Wolniewicz |
| 2006/0253142 A1 | 11/2006 | Bjerken |
| 2007/0021756 A1* | 1/2007 | Kortenbach .......... A61B 17/064 606/151 |
| 2007/0021760 A1 | 1/2007 | Kelleher |

(56) References Cited

U.S. PATENT DOCUMENTS

| | | |
|---|---|---|
| 2007/0112363 A1 | 5/2007 | Adams |
| 2007/0129738 A1 | 6/2007 | Kraemer et al. |
| 2007/0191870 A1 | 8/2007 | Baker et al. |
| 2007/0191871 A1 | 8/2007 | Baker et al. |
| 2007/0219566 A1 | 9/2007 | Gambale |
| 2007/0276409 A1 | 11/2007 | Ortiz et al. |
| 2008/0015618 A1 | 1/2008 | Sonnenschein et al. |
| 2008/0287966 A1 | 11/2008 | Kraemer et al. |
| 2008/0294179 A1* | 11/2008 | Balbierz ............ A61B 17/0643 606/151 |
| 2009/0177214 A1 | 7/2009 | Adams |
| 2009/0198254 A1 | 8/2009 | Laufer et al. |
| 2009/0236388 A1 | 9/2009 | Cole et al. |
| 2010/0241139 A1 | 9/2010 | Harshman |
| 2011/0196391 A1 | 8/2011 | Forsell |
| 2011/0213390 A1 | 9/2011 | Kraemer et al. |

FOREIGN PATENT DOCUMENTS

| | | |
|---|---|---|
| WO | 1999060931 A1 | 12/1999 |
| WO | 2000053102 A1 | 9/2000 |
| WO | 2000078227 A1 | 12/2000 |
| WO | 2001032084 A1 | 5/2001 |
| WO | 2001035834 A1 | 5/2001 |
| WO | 2001064964 A1 | 9/2001 |
| WO | 2001067964 A2 | 9/2001 |
| WO | 2001085034 A1 | 11/2001 |
| WO | 2001089391 A1 | 11/2001 |
| WO | 2002024058 A2 | 3/2002 |
| WO | 2002024080 A2 | 3/2002 |
| WO | 2002028289 A1 | 4/2002 |
| WO | 2002082621 A1 | 10/2002 |
| WO | 2002096327 A2 | 12/2002 |
| WO | 2003061480 A1 | 7/2003 |
| WO | 2003099140 A1 | 12/2003 |
| WO | 2004019787 A2 | 3/2004 |
| WO | 2004019788 A2 | 3/2004 |
| WO | 2004049982 A2 | 6/2004 |
| WO | 2004069055 A2 | 8/2004 |
| WO | 2005065412 A2 | 7/2005 |
| WO | 2005081817 A2 | 9/2005 |
| WO | 2006023764 A2 | 3/2006 |
| WO | 2006034484 A2 | 3/2006 |
| WO | 2006081368 A2 | 8/2006 |
| WO | 2007002817 A2 | 1/2007 |
| WO | 2007064713 A2 | 6/2007 |
| WO | 2010087756 A1 | 8/2010 |

OTHER PUBLICATIONS

Reappraisal of the flap valve mechanism in the gastroesophageal junction: A study of a new valvuloplasty procedure in cadavers; KjellB.A. Thor et al.; Acta Chir Scand 153:25-28, 1987; abstract.
The Plicator Procedure; 1 page; abstract.
Chuttani, MD. et al., "A novel endoscopic full-thickness plicator for treatment of GERD: an animal model study". Gastrointestinal Endoscopy, vol. 56, No. 1, 2002, pp. 116-122; abstract.
Jobe, et al., "Endoscopic Appraisal of the Gastroesophageal Valve After Antireflux Surgery", American Journal of Gastroenterology, ISSN 0002-9270; abstract.
International Search Report for PCT/US2012/054328.

\* cited by examiner

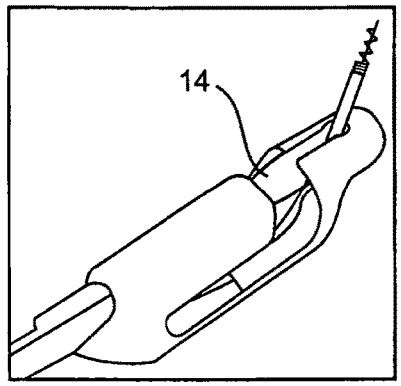
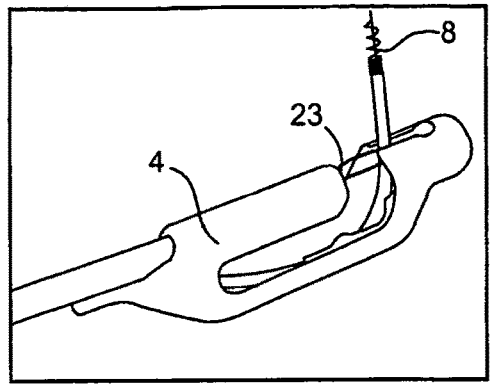
FIG. 4    FIG. 5
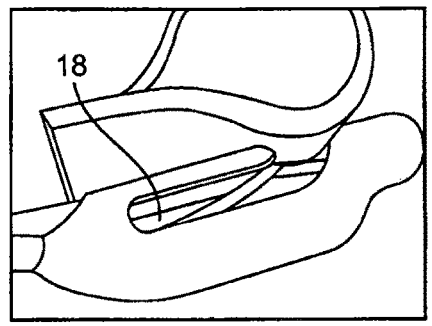
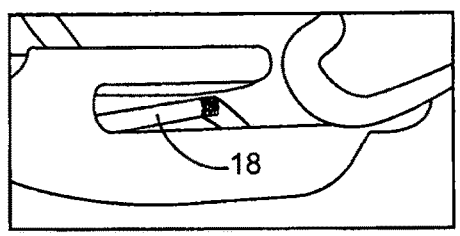
FIG. 6    FIG. 7
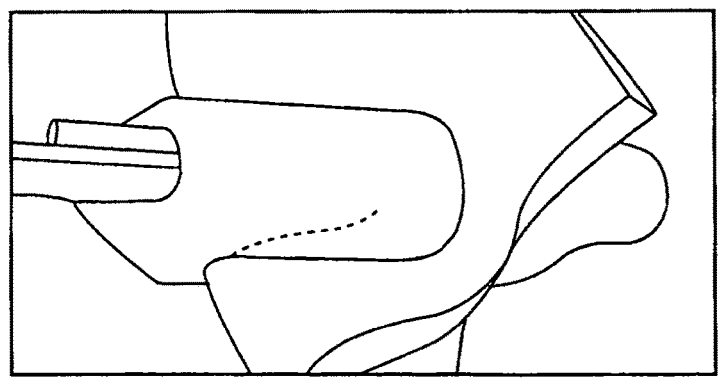
FIG. 8

METHODS AND DEVICES FOR FORMING A TISSUE FOLD

This application is a division of U.S. Ser. No. 12/383,109 filed Mar. 18, 2009, now U.S. Pat. No. 8,906,037, the entire contents of which are incorporated herein by reference.

BACKGROUND

The present invention is directed to methods and devices for approximating tissue and forming a tissue fold.

SUMMARY

The present invention provides a device for forming a tissue fold, which has a mold and a tissue engaging element. The mold has a recess and an opening leading to the recess. Tissue is drawn through the opening and into the mold using the tissue engaging element.

As tissue is drawn into the opening, the tissue forms a fold, which is compressed by the opening. In this manner, the entire fold is drawn through the opening and squeezed and compressed by the opening. The tissue layers are then fastened together to maintain tissue fold.

The opening is positioned at a distal end of the recess so that tissue is drawn proximally through the opening and into the tissue mold. The mold may also have two lateral openings, which communicate with the recess and with the opening at the distal end of the recess. The lateral edges of the tissue fold extend through the lateral openings as the tissue is drawn into the recess.

The tissue engaging element takes a curved path through the tissue mold and changes an angular orientation with respect to the mold by at least 45 degrees when passing through the mold.

The volume of the area around the device, such as the stomach, may also be reduced while drawing the tissue into the recess.

These and other aspects of the present invention will become apparent from the following description of the preferred embodiment.

DESCRIPTION OF DRAWINGS

FIG. 4 shows a tissue engaging element extending from a mold.

FIG. 5 shows the tissue engaging element positioned to engage tissue.

FIG. 6 shows the tissue engaging element engaged with tissue and the tissue drawn toward the mold.

FIG. 7 shows the tissue fold just before entering the mold.

FIG. 8 shows the tissue drawn into the recess and a fastener applied to maintain the tissue fold.

DESCRIPTION OF THE PREFERRED EMBODIMENTS

Figure 1:
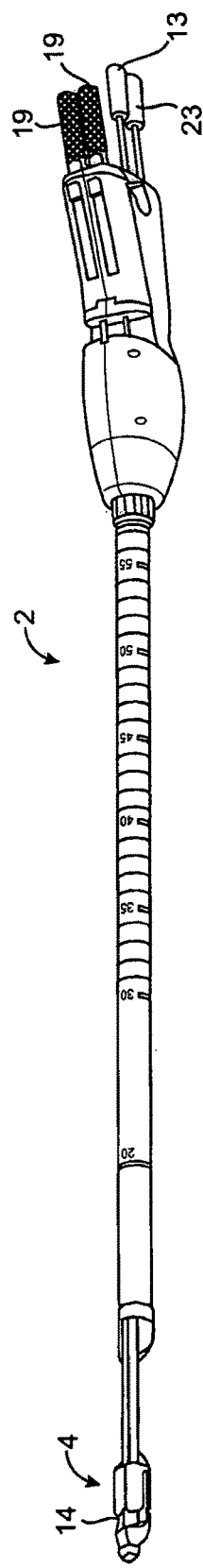
FIG. 1 shows a device for forming a tissue fold.
Figure 2:
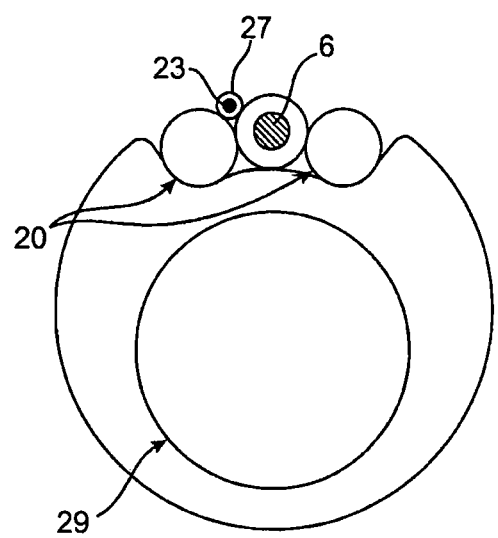
FIG. 2 shows a cross-sectional view of the device.
Figure 3:
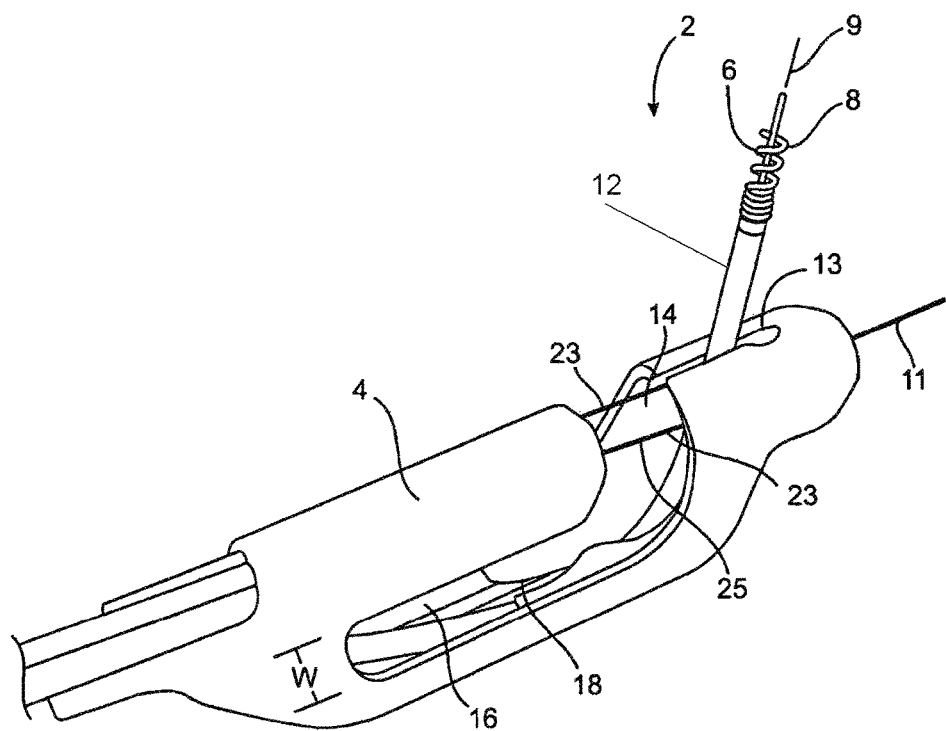
FIG. 3 shows a distal end of the device.

Referring to FIGS. 1-3, a device 2 for forming a tissue fold is shown. The device 2 has a tissue mold 4 and a tissue engaging element 6 which draws tissue into the mold 4.

The tissue engaging element 6 has a helical coil 8 with a sharp tip 10 which is rotated into engagement with tissue. The device 2 may include any other suitable mechanism for engaging tissue such as a hook, barb, or suction element. The tissue engaging element 6 is coupled to a cable 12 which may be rotated and translated in the manner described below to manipulate the element 6. The tissue engaging element 6 extends though a slot 13 in the body which stabilizes the element 6 and permit's the user to steer the element 6 with the mold 4. The coil 8 is initially directed somewhat laterally from the mold 4 as shown in FIG. 5. As the coil 8 moves into the mold 4, the coil 8 takes a curved path through the mold 4 so that a longitudinal axis 9 of the coil 8 changes angular orientation with respect to a longitudinal axis 11 of the mold by at least 45 degrees. A manipulator 13 extends from the proximal end of the device 2 and is used to move and rotate the coil 8. A lock (not shown) is used to lock rotation of the manipulator 13 (and coil 8) as described below in connection with the method of using the device 2.

The tissue mold 4 has an opening 14 which is relatively small so that the tissue fold is compressed and squeezed as the tissue enters the tissue mold 4. An advantage of the present invention is that squeezing the tissue in this manner may help to separate the tissue creating the fold from surrounding tissue. Such connections or adhesions to other tissue may not be desirable. An advantage of the present invention is that squeezing and compressing the tissue fold during introduction into the mold may help to reduce such connections and adhesions.

The tissue mold 4 has a recess 16 which receives the tissue fold. The recess 16, as shown in FIG. 3, is defined by a fixed volume, i.e., the recess 16 does not expand or contract when receiving tissue. Two lateral openings 18 communicate with the recess 16 and with the opening 14. As the tissue is drawn into the mold 4, the lateral edges of the tissue fold extend through the openings 18 as shown in FIG. 8. The lateral openings 18 are generally L-shaped but may take any other suitable shape. The opening 14 leading to the recess 16 is at the distal end of the recess 16 so that the tissue is drawn proximally through the device 2. A width W of the lateral openings 14 may be relatively uniform over the length of the lateral openings 14 so that the lateral openings 14 can maintain a relatively uniform pressure on the tissue fold once the tissue enters the mold 4 and while it is drawn further into the recess 16.

One or more lumens 20 extends through the device 2 and are used to deliver one or more fasteners 22 to maintain the tissue fold (see FIGS. 2 and 8). The fastener 22 may be any suitable fastener and one such fastener 22 is described in U.S. Ser. No. 10/949,737, which is incorporated herein by reference. A proximal end 19 of the fastener extends from the device for manipulation by the user.

A centering mechanism 23 is also provided for centering and manipulating the tissue engaging element 6. The centering mechanism 23 may be a wire loop 25 which is looped around the element 6. The wire loop 25 may be tensioned to move the tissue engaging element 6 from the position of FIG. 4 to the position of FIG. 5 in which the element 6 is oriented substantially perpendicular to the longitudinal axis of the device 2. The wire loop 25 extends through a lumen 27 as shown in the cross-sectional view of FIG. 2. The tissue engaging element 6 is free to slide within the wire loop 25, however, the wire loop is not large enough to permit the coil to pass therethrough so that the wire loop 25 is eventually drawn back with the tissue engaging element 6.

Use of the device 2 is now described with reference to FIGS. 3-8. The following method relates to use in the stomach but the device 2 may find uses in other areas as well without departing from the scope of the invention. The device 2 is introduced down the patient's throat to the desired location for creating a tissue fold. An endoscope (not shown) is used to guide the device 2 to the desired location and is introduced through a lumen 29. The device 2 may pass through the endoscope or the two may extend side by side as is known in the art without departing from the scope of the invention. The centering mechanism 23 is then tensioned to move the element 6 to the position of FIG. 5 so that the coil 8 is perpendicular to the longitudinal axis of the mold. The helical coil 8 is then rotated into engagement with tissue. Once engaged with tissue, the coil 8 and tissue are permitted to return to their respective free states rotationally. The helical coil 8 is then locked against rotation in preparation for manipulating the tissue as described below.

The mold 4 is then oriented so that it will create a fold, which is aligned in the desired direction. The area around the device 2 may then be reduced in volume using vacuum. The lumen 20, lumen 29 or another independent lumen or device may be used to evacuate air from the area around the device 2. The helical coil 8 is then slowly drawn back into the mold 4 while the area around the device 2 is reduced in volume. As the tissue enters the mold 4, the tissue fold is compressed as it enters the opening 14 so that the entire fold is compressed and drawn through the relatively small opening 14. In this manner, tissue connections and adhesions on the far side of the tissue layers, which form the tissue fold may be released prior to forming the fold.

The coil 8 is then moved proximally to draw the tissue through the opening 14 and into the recess 16. As the coil 8 continues to draw the tissue into the recess 16, the lateral edges of the tissue extend through the lateral openings 18. One or more of the fasteners 22 are then deployed through the lumen 20 to secure the tissue fold.

The present invention has been described with respect to a preferred embodiment, however, it is understood that numerous modifications and alterations could be made without departing from the scope of the invention. For example, the lateral openings could be linear rather than curved and the fastener may be an adhesive rather than a mechanical fastener.

What is claimed is:

1. A device for forming a tissue fold, comprising:
    a stationary mold having a fixed volume recess and an opening leading to the recess;
    an elongated slot having a distal end and a proximal end, the proximal end of the elongated slot being adjacent to a distal end of the recess;
    a cable having a helical coil at a distal end of the cable and being housed within the recess and configured to engage tissue, the helical coil being movable outside the fixed volume recess by extending through the elongated slot located distally of the opening leading to the fixed volume recess to engage tissue and to draw tissue through the opening and into the fixed volume recess;
    a centering mechanism disposed in the slot and looped around the cable to move the cable to a position substantially perpendicular to a longitudinal axis of the stationary mold; and
    wherein the opening is sized so that tissue drawn through the opening by the helical coil is compressed as the tissue fold enters the tissue mold.

2. The device of claim 1, further comprising:
    a fastener positioned to fasten together a tissue fold contained within the fixed volume recess.

3. The device of claim 1, wherein
    the opening is at a distal end of the fixed volume recess; and
    the helical coil is configured to draw the tissue proximally into the tissue mold.

4. The device of claim 1, wherein:
    the mold has two lateral openings, which communicate with the fixed volume recess and with the opening.

5. The device of claim 4, wherein:
    the lateral openings have a substantially uniform width.

6. The device of claim 4, wherein
    the lateral openings are L-shaped.

7. The device of claim 1, wherein:
    the cable and helical coil traverse a curved path within the tissue mold.

8. The device of claim 1, wherein:
    the cable and helical coil change in angular orientation with respect to a longitudinal axis of the tissue mold by at least 45 degrees when the cable and helical coil are moved through the mold.

9. The device of claim 1, wherein the centering mechanism is a wire loop wrapped around the cable.

10. The device of claim 9, wherein the cable freely slides through the wire loop, but the helical coil is larger than the wire loop and will not pass therethrough.

* * * * *